United States Patent
Nath

[11] 3,995,934
[45] Dec. 7, 1976

[54] FLEXIBLE LIGHT GUIDE

[76] Inventor: Günther Nath, Speyererstrasse 21, 8000 Munich 40, Germany

[22] Filed: Oct. 15, 1974

[21] Appl. No.: 514,954

[30] Foreign Application Priority Data
Oct. 19, 1973  Germany .......................... 2352670
July 11, 1974  Germany .......................... 2433219

[52] U.S. Cl. .......................... 350/96 LM; 250/495; 350/96 R
[51] Int. Cl.² .......................... G02B 5/14
[58] Field of Search .................... 350/96 R, 96 LM; 250/492, 495

[56] References Cited
UNITED STATES PATENTS
3,770,350  11/1973  Stone et al. .................. 350/96 LM
3,793,541  2/1974  Ashkin et al. ................ 350/96 LM OTHER PUBLICATIONS
Liquid Optical Fibers, by G. W. Taylor, from Applied Optics, vol. 11, No. 4, Apr. 1972, pp. 786–790.

Primary Examiner—Archie R. Borchelt
Attorney, Agent, or Firm—William R. Woodward

[57] ABSTRACT

A flexible light guide of the liquid filled type is provided with a liquid supply container outside the light guide.

14 Claims, 4 Drawing Figures

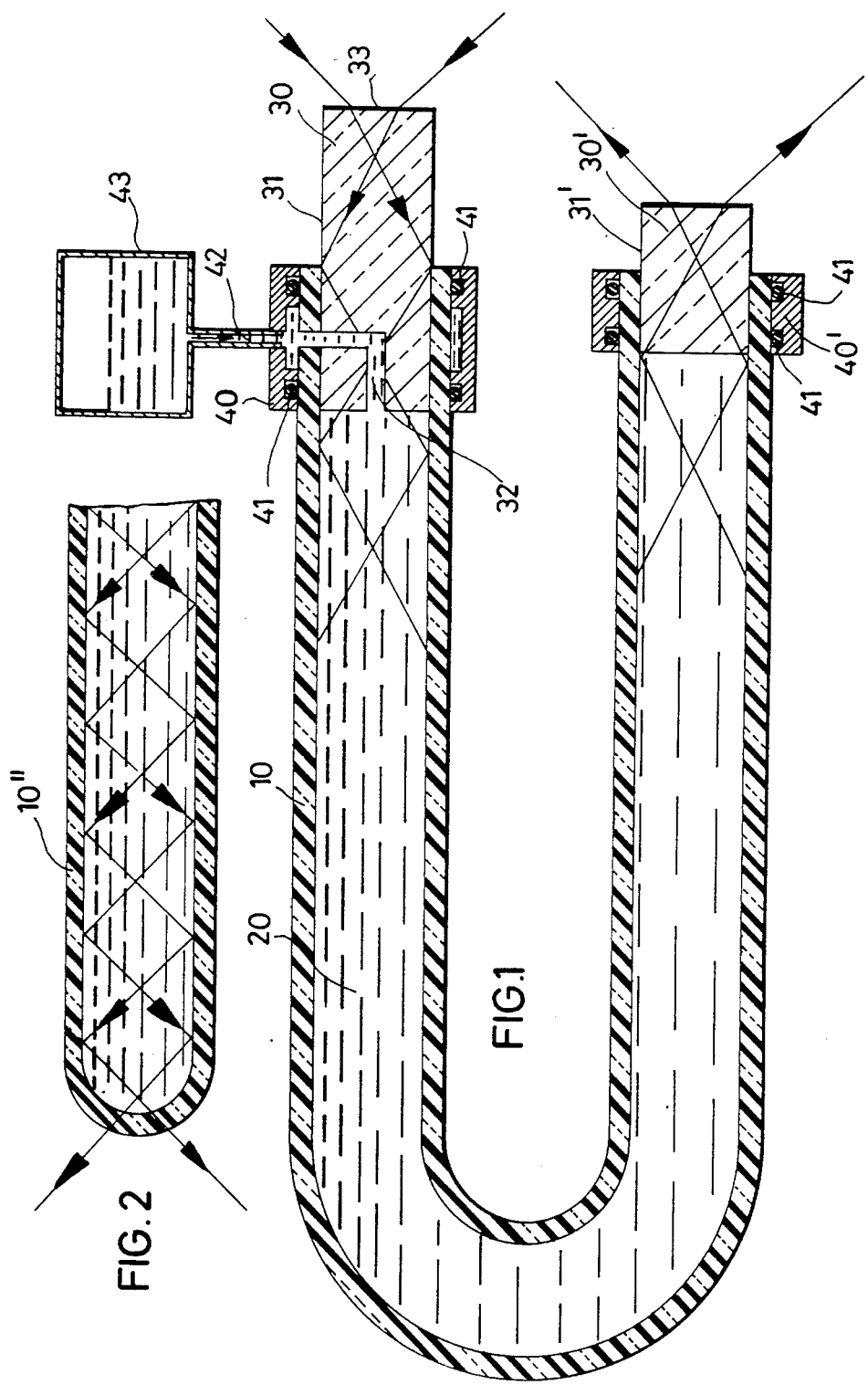

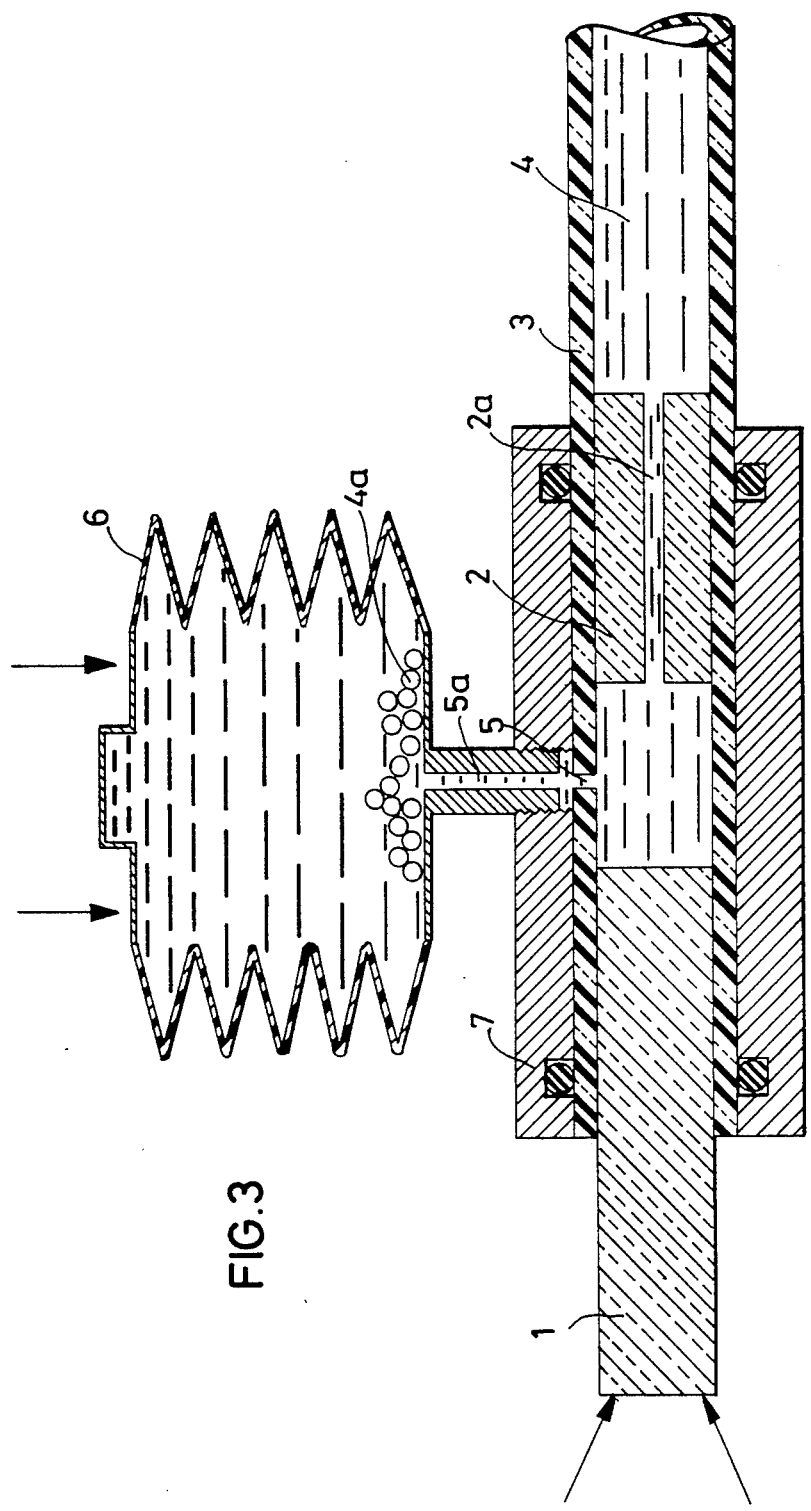

FLEXIBLE LIGHT GUIDE

BACKGROUND OF INVENTION

1. Field to which invention relates

The present invention relates to a flexible light guide, and more particularly to a light guide in the case of which the light is transmitted through an elongated liquid column operating as a "light guide or optic fiber", and surrounded by a flexible tube of plastics material.

2. The prior art

Known light guides of this type have the disadvantage that their transmission becomes poorer in the course of time. It has been found that this is to a large extent due to the fact that the light conducting liquid wets the material of the flexible tube and diffuses out through the usually relatively thin wall of the plastics material flexible tube so that small gas bubbles are produced in the tube, which disperse or diffuse the light and reduce transmission.

SUMMARY OF INVENTION

Accordingly one aim of the present invention is that of providing a flexible light guide of the above-mentioned type, whose transmission remains at a high value even over long periods of time and even in the case of the transmission of high power radiation.

Furthermore, the invention is intended to provide a flexible light guide, which has a high transmission in the visible spectral range, in the near infrared and possibly also in the near ultraviolet, and also more particularly in the spectral range between approximately 0.6 and 0.35 microns (in accordance with the liquid used) and approximately 3.2 microns so that it is particularly suitable for use with a tungsten incandescent lamp as a light source, whose colour temperature as is known lies between approximately 2000 and 3500 K, or also with an Nd-YAG-laser.

In accordance with one form of the invention a flexible light guide has a column, operating as an optic fiber, of a liquid, which absorbs as little as possible of the wavelength range to be transmitted, with a predetermined index of refraction and surrounded by a flexible tube of plastics material, which in the wavelength range to be transmitted has a somewhat lesser index of refraction than the liquid; in accordance with the invention such a light guide has a supply container filled at least partly with the liquid and connected with the interior of the flexible tube.

The presence of the supply container ensures that the flexible tube is always completely filled with the light conducting liquid even in the course of time liquid should be lost from the flexible tube. The supply container furthermore ensures satisfactory filling of the flexible tube and high transmission of the light guide even on bending of the flexible tube and in the case of high thermal loading of the liquid column owing to high intensities of radiation.

LIST OF SEVERAL VIEWS OF DRAWINGS

Further objects, features and advantages of the invention will be discussed in the following description of particular embodiments of the principle of the invention as shown in the accompanying drawings.

FIG. 1 of these drawings is a diagrammatic sectional view of a first embodiment of the invention.

FIG. 2 is a sectional view of one end of a second embodiment of the invention.

FIG. 3 is a sectional view of a part of a preferred embodiment of the invention.

DESCRIPTION OF PREFERRED EMBODIMENTS

Figure 4:
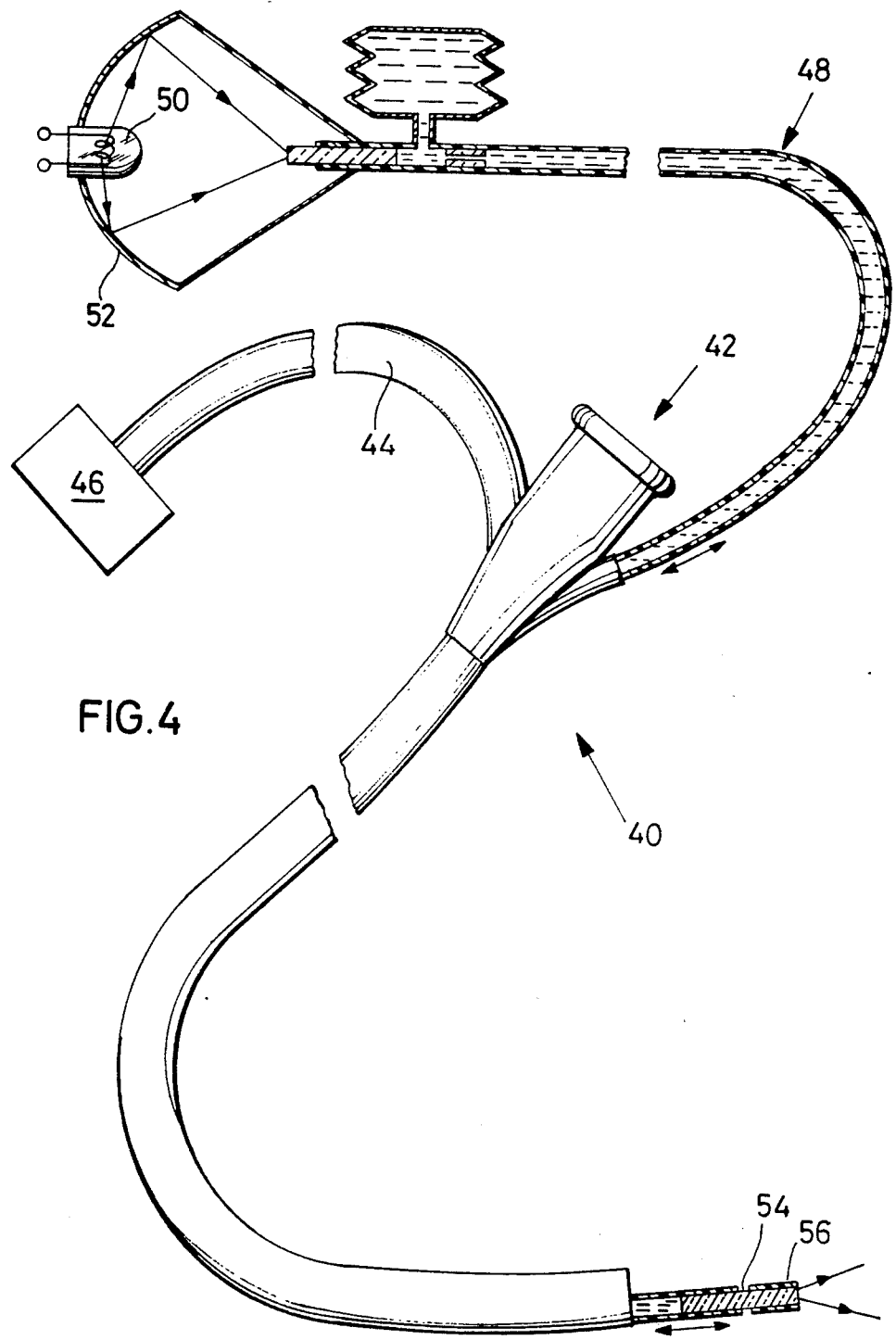
FIG. 4 is a diagrammatic representation of an endoscope, which comprises a coagulating device with a light guide in accordance with the invention.

The embodiment of the light guide shown in FIG. 1 and in accordance with the invention comprises a flexible tube 10 of flexible plastics material, which is filled with a liquid 20 and at the ends is sealed or closed by cylindrical windows 30 and 30' made of a material which has a high transparency for the radiation to be transmitted.

The index of refraction of the liquid 20 can be approximately one tenth higher than that of the plastics material of the tube so that an aperture angle of approximately 70° is reached.

Typical dimensions for the flexible tube 10 are for example: length 150 cm, internal diameter 1 to 5 mm, and wall thickness 0.3 to 0.5 mm.

The inner wall of the flexible tube should be as smooth and mirror-like as possible and the material should have the highest possible transparency for the radiation to be transmitted.

As a material for the flexible tube 10 it is possible in principle to use any flexible plastics materials, which comply with the above conditions and which are compatible with the liquid. It is preferred to use carbon-fluorine polymers. Plastics materials of this type are commercially available under the trade names Teflon, FEP, Neoflon, Hostaflon, PTFE and the like. Particularly satisfactory have been found the thermoplastic materials Teflon FEP (polytetrafluoroethylene hexafluoropropylene) and Teflon PFA (perfluoroalkoxy).

As the liquid 20 it has been found particularly suitable to use organic liquids, which comprise elements of the Groups IV–VII of the Periodic System, that is to say relatively heavy elements, if it is desired to provide for good transmission in the near IR range. Particularly suitable are organic liquids; they should as far as possible contain no CH- or OH-groups and should have a solubility for $H_2O$ which is as low as possible.

For a flexible tube 10 of Teflon FEP (registered trade mark) it has been found particularly suitable to use $CCl_4$ ($n_D = 1.47$), which should be as pure as possible in order to keep down absorption.

Besides $CCl_4$ other possible liquids for IR light guides are $C_2Cl_4$, $C_4Cl_6$, $C_5Cl_6$ (hexachlorobutadiene), $C_3Cl_6O$ (hexachloroacetone), $Si_2OCl_6$ (hexachlorodisiloxane), $C_3Cl_6$ (hexachloropropene), $C_4F_2Cl_8$ (1,4-difluorooctochlorobutane), $PCl_2$ (phosphorus dichloride), $P(SCN)_3$; and furthermore $SiCl_4$, $Si_2Cl_4$, $(C_2ClF_3)_n$, the compounds known as "Freons"; for the visible spectral range and the near UV range it is also possible to use alcohols as for example benzyl alcohol, butanol, pentanol etc., and furthermore silicone oils, liquid paraffine and others.

For less demanding work the flexible tube 10 can also be made of polytrifluorochloroethylene, polyvinyl chloride, 4-methyl-pentene-1, polymethylpentene, polyethylene, polypropylene, polycarbonate and the like, that is to say in general of a polymer which is made up principally of elements in the group C, Si, H, Cl, F, O and N.

The liquid can also consists of a mixture of two or more of the above-mentioned compounds.

As a material for the windows 30 and 30' it has been found particularly suitable to use SiO$_2$, more particularly in the form of quartz glass, which as far as possible should be free of OH-ions. A suitable material is for example the material known as "Infrasil" as commercially available.

The cylindrical casing surface of the window is preferably fire-polished and can furthermore carry a dielectric layer 31 or 31', respectively, with a thickness of several microns and consisting of vapour-deposited MgF$_2$. The two end surfaces of the window are plane-polished. The windows can also be produced from other dielectric materials which are transparent to IR, as for example CaF$_2$.

The windows have an outer diameter, which corresponds generally to the inner diameter of the flexible tube 10. The tube is pressed at its ends by a respective clamping device against the respective window. The clamping devices comprise a cylindrical sleeve 40 and 40', which internally adjacent to their ends have two annular grooves so that each can accommodate an O-ring 41. The sleeves with the grooves and the O-rings are so dimensioned that the end of the flexible tube is pressed in a sealing manner against the window and is held on the window.

The O-rings 41 consist preferably of white, non-absorbent material. The sleeves 40 and 40' are preferably given an internal mirror finished or they consist of Teflon or the like.

The window 30 has a hole which communicates for the liquid 20 and which firstly runs generally axially and then runs radially and is connected with a central annular groove in the sleeve 40. This annular groove is connected via a capillary tube 42 with a supply container 43. The space formed by the hole 32, the annular groove in the sleeve 40, the capillary tube 42, and the supply container 43 is filled at least partly with the light conducting liquid so so that the liquid can flow into the flexible tube 10 to top it up and the tube always remains completely filled with liquid, even if liquid should evaporate through the wall of the tube or should be lost in another manner or if the light guide should be exposed to substantial variations in temperature. The liquid supply need not be very large if instead of liquid such as CCl$_4$, which readily evaporate, a viscous liquid with a high boiling point as for example hexachlorobutadiene is used.

If the window 30 serves as a light passage window and if on its front surface 33 the radiation of an intensive light source is focussed, this window will then preferably have a length of 10 to 20 cm and will extend correspondingly far out of the flexible tube in order to prevent excessive heating of the clamping device 40 and 41.

FIG. 2 shows a form, particularly suitable for endoscopic applications, of the (front) light exit end of a light guide in accordance with the invention. The light guide comprises a liquid filled plastics flexible tube 10'', which at the front end, where the light emerges, is sealed by fusing and consists of a plastics material with the highest possible transparency, as for example of carbon fluorine polymer, such as Teflon FEP of Teflon PFA.

The preferred embodiment of the invention shown in FIG. 3 comprises, like the above-mentioned light guides, a flexible tube 3, which is provided with a liquid 4. The light entry end, shown in FIG. 3, of the light guide has a two-part inlet window, whose first part 1 consists of a cylindrical quartz rod while the second part 2 is completely plugged into the flexible tube 3 and is formed by a piece of quartz tube. The flexible tube 3 is pressed by a clamping device of the above-described type with a sleeve 7 in a sealing manner against the window parts 1 and 2.

The liquid 4 in the flexible tube 3 is connected via a hole 5 in the flexible tube and a fine tube 5a with an external liquid supply container 6, which is formed by an elastic resilient bellows. The supply container 6 is preferably completely filled with liquid and can also comprise insoluble additives 4a for the liquid, as for example drying materials adapted to take up water.

Other possible additives are materials for absorbing in order to keep the liquid pure. Instead of an elastic liquid supply container it is also possible to provide a supply container with rigid walls, which is filled partly with a gas under pressure. The use of such an arrangement serves to keep constant the pressure, acting upon the liquid 4 in the flexible tube 3, despite variations in temperature and the like so that variations in density and transmission, which might reduce the transmission, are avoided.

FIG. 4 shows a principally conventional endoscope 40 with an observation eyepiece 42 and an optic fiber light guide 44 serving for illumination. The optic fiber 44 is connected with an illuminating unit 46. In the instrument or biopsy channel of the endoscope a light guide 48 is provided, which in essential respects is the same as the embodiment of the invention in accordance with FIG. 3 and comprises a liquid which has a high transparency for IR radiation at the light inlet end there is arranged a 150 W-tungsten filament incandescent lamp 50 with a gold reflector 52 with suitable optical coupling with the inlet end. (As a light source it is as an alternative possible to use an Nd-YAG-laser for example.)

The light guide 48 has a cylindrical light outlet window 54 of quartz glass, on whose outer end a cap 56 (or a coating) of a carbon fluorine polymer with a highest possible transparency is arranged and which is made preferably of Teflon FEP of Teflon PFA. Instead of the window arrangement 54-56 it is possible to make use of a flexible tube end which is sealed by fusing, as is shown in FIG. 2. In operation the window 54 is pressed with the end side of the cap 56 on a haemorrhage so that the blood is coagulated by the transmitted heat radiation and bleeding is stopped. The cap prevents sticking of the light guide on the coagulated tissue.

What I claim is:

1. An instrument for use with a source of infra red radiation for applying radiation within a living body for medical purposes comprising a flexible light guide which comprises a column of a liquid having a predetermined refractive index and selected to absorb as little as possible of the wavelength range of said radiation, a flexible tube, surrounding and containing the liquid, of plastics material which has a refractive index somewhat smaller than that of the liquid in the wavelength range to be transmitted and is provided with a liquid-tight window at one end fashioned in a manner suitable for insertion into a living body and another liquid-tight window at the other end, said other end being fashioned in a manner suitable for receiving radiation from a radiation source outside the living body, the liquid in said tube being at rest, and a liquid supply container which is located near the radiation receiving end of said tube and is connected via a liquid duct with the interior of the flexible tube.

2. An instrument for applying radiation for medical purposes in accordance with claim 1, characterised in that the liquid supply container is a closed supply container.

3. An instrument for applying radiation for medical purposes in accordance with claim 2, characterized in that the liquid container has means for putting the liquid under pressure.

4. An instrument for applying radiation for medical purposes in accordance with claim 2, characterised in that the supply container has an elastic wall.

5. An instrument for applying radiation for medical purposes in accordance with claim 1, characterised in that the liquid supply container comprises a purification treatment medium for the liquid.

6. An instrument for applying radiation for medical purposes in accordance with claim 1, characterised in that the liquid supply container comprises a drying medium.

7. An instrument for applying radiation for medical purposes in accordance with claim 1, characterised in that the flexible tube consists of a carbon polymer.

8. An instrument for applying radiation for medical purposes in accordance with claim 1, characterized in that the flexible tube consists of a material selected from the group: polyvinyl chloride, 4-methyl-pentene-1, polymethylpentene, polyethylene, polypropylene and polycarbonate and solid silicone.

9. An instrument for applying radiation for medical purposes in accordance with claim 1, characterised in that the liquid comprises at least one of the following compounds: $CCl_4$, $C_2C_4$, $C_4Cl_6$, $SiCl_4$, $SiCl_6$, $(C_2ClF_3)_n$, $C_5Cl_6$, $C_3Cl_6O$, $Si_2OCl_6$, $C_4F_2Cl_8$; 1, 4-difluorooctochlorobutane, $PCl_2$; $P(SCN)_3$, a liquid aliphatic or aromatic alcohol, liquid paraffin.

10. An instrument for applying radiation for medical purposes in accordance with claim 1, characterised in that at least one of its ends is provided with a window of quartz glass.

11. An instrument for applying radiation for medical purposes in accordance with claim 1, characterised in that the insertion end of the flexible tube is sealed by fusing.

12. An instrument for applying radiation for medical purposes in accordance with claim 1, characterised by a light exit end with a window plugged at least partly into the flexible tube; a clamping device pressing the flexible tube in a sealing manner onto the window; a body having an axial duct and consisting of a material with a minimum light absorption and arranged in the flexible tube with a spacing from the window, the material being connected in a sealing manner with the flexible tube by a second clamping device; and by the presence of a hole in the wall of the flexible tube between the two clamping devices, the hole forming a part of the liquid duct.

13. An instrument for applying radiation for medical purposes in accordance with claim 10, characterised in that the flexible light guide thereof is arranged in the biopsy duct of an endoscope.

14. An instrument for applying radiation for medical purposes in accordance with claim 13, characterised by a light exit window of quartz glass, on whose light outlet surface a layer of a carbon-fluorine polymer is arranged.

* * * * *